(12) United States Patent
Shehada et al.

(10) Patent No.: US 9,945,848 B2
(45) Date of Patent: Apr. 17, 2018

(54) REAGENT CALIBRATION SYSTEM AND METHOD

(71) Applicant: Becton, Dickinson and Company, Franklin Lakes, NJ (US)

(72) Inventors: Ramez Emile Necola Shehada, La Mirada, CA (US); Oliver Crespo-Diaz, San Jose, CA (US); Paul Limb, Burlingame, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 15/300,034

(22) PCT Filed: Feb. 5, 2015

(86) PCT No.: PCT/US2015/014681
§ 371 (c)(1),
(2) Date: Sep. 28, 2016

(87) PCT Pub. No.: WO2015/160420
PCT Pub. Date: Oct. 22, 2015

(65) Prior Publication Data
US 2017/0176425 A1 Jun. 22, 2017

Related U.S. Application Data

(60) Provisional application No. 61/979,300, filed on Apr. 14, 2014.

(51) Int. Cl.
*G01N 15/10* (2006.01)
*G01N 15/14* (2006.01)
(Continued)

(52) U.S. Cl.
CPC ... *G01N 33/54313* (2013.01); *G01N 15/1012* (2013.01); *G01N 15/1429* (2013.01);
(Continued)

(58) Field of Classification Search
CPC .......... G01N 33/54313; G01N 33/543; G01N 33/50; G01N 33/48; G01N 15/1012; G01N 15/10; G01N 15/00
(Continued)

(56) References Cited

U.S. PATENT DOCUMENTS 4,845,653 A 7/1989 Conrad et al.
5,627,040 A 5/1997 Bierre et al.
(Continued)

FOREIGN PATENT DOCUMENTS

EP 2 711 713 3/2014
EP 2 843 418 3/2015
(Continued)

OTHER PUBLICATIONS

Urankar et al, English Machine Translation of FR 2 994 740 of Description. Obtained on Nov. 8, 2017 from Espacenet. (Year: 2017).*

(Continued)

*Primary Examiner* — Christine T Mui
(74) *Attorney, Agent, or Firm* — Knobbe Martens Olson & Bear LLP (57) ABSTRACT

One aspect relates to a method of calibrating event data. The method includes obtaining, via an electronic device including a processor, event data for an assay including a reagent. The reagent is associated with one of a plurality of manufacturing lots of the reagent. The method includes receiving one or more calibration factors for the reagent based on an identifier associated with the one of the plurality of manufacturing lots. The method further includes generating calibrated event data based on an application of the one or more calibration factors to the event data.

18 Claims, 7 Drawing Sheets

(51) Int. Cl.
- *G01N 33/543* (2006.01)
- *G01N 35/00* (2006.01)
- *G01N 21/64* (2006.01)
- *G01N 21/01* (2006.01)
- *G01N 15/00* (2006.01)

(52) U.S. Cl.
CPC ......... *G01N 15/1459* (2013.01); *G01N 21/64* (2013.01); *G01N 35/00693* (2013.01); *G01N 2015/0065* (2013.01); *G01N 2015/1006* (2013.01); *G01N 2015/1402* (2013.01); *G01N 2035/00673* (2013.01); *G01N 2035/00702* (2013.01); *G01N 2201/127* (2013.01)

(58) Field of Classification Search
USPC ........................................................ 436/172
See application file for complete search history.

(56) References Cited

U.S. PATENT DOCUMENTS

| | | | |
|---|---|---|---|
| 5,739,000 | A | 4/1998 | Bierre et al. |
| 5,795,727 | A | 8/1998 | Bierre et al. |
| 5,962,238 | A | 10/1999 | Sizto et al. |
| 6,014,904 | A | 1/2000 | Lock |
| 6,944,338 | B2 | 9/2005 | Lock et al. |
| 2008/0240988 | A1 | 10/2008 | Wakamiya et al. |
| 2009/0142231 | A1 | 6/2009 | Shibuya et al. |
| 2012/0245889 | A1 | 9/2012 | Zhu et al. |

FOREIGN PATENT DOCUMENTS

| | | | |
|---|---|---|---|
| FR | 2 994 740 A1 * | 2/2014 | ............ G01N 21/64 |
| WO | WO 2013/134491 | 9/2013 | |
| WO | WO 2014/029743 | 2/2014 | |

OTHER PUBLICATIONS

Bauer et al. (eds.), Clinical Flow Cytometry: Principles and Applications, Williams & Wilkins (Jan. 1993).
Jaroszeski et al. (eds.), Flow Cytometry Protocols, Methods in Molecular Biology No. 91, Humana Press (Nov. 1997).
Landay et al. (eds.), Clinical Flow Cytometry, Annals of the New York Academy of Sciences vol. 677 (Mar. 1993).
Ormerod (ed.), Flow Cytometry: A Practical Approach, Oxford Univ. Press (Aug. 1997).
Pawley (ed.), Handbook of Biological Confocal Microscopy, 2nd Edition, Plenum Press (Aug. 1989).
Shapiro Practical Flow Cytometry, 4th ed., Wiley-Liss (Jul. 2003).
International Search Report for International Application No. PCT/US2015/014681 dated Apr. 15, 2015.

* cited by examiner

REAGENT CALIBRATION SYSTEM AND METHOD

CROSS REFERENCE TO RELATED APPLICATIONS

This application is the national phase of PCT Application No. PCT/US2015/014681, filed on Feb. 5, 2015, which claims the benefit of U.S. Provisional Application No. 61/979,300, filed on Apr. 14, 2014, each of which are incorporated herein by reference in their entirety.

This disclosure relates to assay reagent calibration, and in particular to reagent based calibration of quantitative results as flow cytometer mean fluorescence intensity results.

Particle analyzers, such as flow and scanning cytometers, are analytical tools that enable the characterization of particles on the basis of optical parameters such as light scatter and fluorescence. In a flow cytometer, for example, particles, such as molecules, analyte-bound beads, or individual cells, in a fluid suspension are passed by a detection region in which the particles are exposed to an excitation light, typically from one or more lasers, and the light scattering and fluorescence properties of the particles are measured. Particles or components thereof typically are labeled with fluorescent dyes to facilitate detection. A multiplicity of different particles or components may be simultaneously detected by using spectrally distinct fluorescent dyes to label the different particles or components. In some implementations, a multiplicity of photodetectors, one for each of the scatter parameters to be measured, and one for each of the distinct dyes to be detected are included in the analyzer. The data obtained comprise the signals measured for each of the light scatter parameters and the fluorescence emissions.

Cytometers may further comprise means for recording the measured data and analyzing the data. For example, data storage and analysis may be carried out using a computer connected to the detection electronics. For example, the data can be stored in tabular form, where each row corresponds to data for one particle, and the columns correspond to each of the measured parameters. The use of standard file formats, such as an "FCS" file format, for storing data from a flow cytometer facilitates analyzing data using separate programs and/or machines. Using current analysis methods, the data typically are displayed in 2-dimensional (2D) plots for ease of visualization, but other methods may be used to visualize multidimensional data.

The parameters measured using a flow cytometer typically include the excitation light that is scattered by the particle along a mostly forward direction, referred to as forward scatter (FSC), the excitation light that is scattered by the particle in a mostly sideways direction, referred to as side scatter (SSC), and the light emitted from fluorescent molecules in one or more channels (range of frequencies) of the spectrum, referred to as FL1, FL2, etc., or by the fluorescent dye that is primarily detected in that channel. Different cell types can be identified by the scatter parameters and the fluorescence emissions resulting from labeling various cell proteins with dye-labeled antibodies.

Both flow and scanning cytometers are commercially available from, for example, BD Biosciences (San Jose, Calif.). Flow cytometry is described in, for example Landy et al, (eds.), Clinical Flow Cytometry, Annals of the New York Academy of Sciences Volume 677 (1993); Bauer et al. (eds.), Clinical Flow Cytometry: Principles and Applications, Williams & Wilkins (1993); Ormerod (ed.), Flow Cytometry: A Practical Approach, Oxford Univ. Press (1997); Jaroszeski et al. (eds.), Flow Cytometry Protocols, Methods in Molecular Biology No. 91, Humana Press (1997); and Practical Shapiro, Flow Cytometry, 4th ed., Wiley-Liss (2003); all incorporated herein by reference, Fluorescence imaging microscopy is described in, for example, Pawley (ed.), Handbook of Biological Confocal Microscopy, 2nd Edition, Plenum Press (1989), incorporated herein by reference.

The data obtained from an analysis of cells (or other particles) by multi-color flow cytometry are multidimensional, wherein each cell corresponds to a point in a multi-dimensional space defined by the parameters measured. Populations of cells or particles are identified as clusters of points in the data space. The identification of clusters and, thereby, populations can be carried out manually by drawing a gate around a population displayed in one or more 2-dimensional plots, referred to as "scatter plots" or "dot plots," of the data. Alternatively, clusters can be identified, and gates that define the limits of the populations, can be determined automatically. Examples of methods for automated gating have been described in, for example, U.S. Pat. Nos. 4,845,653; 5,627,040; 5,739,000; 5,795,727; 5,962,238; 6,014,904; 6,944,338; and U.S. Pat. Pub. No. 2012/0245889, each incorporated herein by reference.

It will be appreciated that due, in part, to the scale at which flow cytometers operate, even minor variations can have significant impacts on the resulting data. Variations can be introduced based on the reagent used, the manufactured lot of the reagent used, conditions when the reagent is used (e.g., temperature, humidity, barometric pressure), instrument used to generate the data, and so on. These variables can lead to confusion in interpreting the results as a given population cluster which is identified during a first test may appear in a different location, or not at all, in a subsequent test. As such, it is desirable to provide a reliable way to generate reproducible event data results that may also be reliably compared with past or future data.

SUMMARY

The systems, methods, and devices of the disclosure each have several innovative aspects, no single one of which is solely responsible for the desirable attributes disclosed herein.

In one innovative aspect, a method is provided. The method includes obtaining, via an electronic device including a processor, event data for an assay including a reagent. The reagent is associated with one of a plurality of manufacturing lots of the reagent. The method includes receiving one or more calibration factors for the reagent based on an identifier associated with the one of the plurality of manufacturing lots. The method further includes generating calibrated event data based on an application of the one or more calibration factors to the event data.

In another innovative aspect, a calibration device is provided. The device includes an event data receiver configured to receive event data for an assay including a reagent associated with one of a plurality of manufacturing lots. The device also includes a calibrator configured to obtain one or more calibration factors for the reagent based on an identifier associated with the one of the plurality of manufacturing lots. The device further includes an event data processor configured to generating calibrated event data based on an application of the one or more calibration factors to the event data, In a further innovative aspect, a non-transitory computer readable medium comprising instructions executable by a processor of an apparatus is provided to perform one or more of the innovative methods described herein.

In yet another innovative aspect, an apparatus comprising a processor, configured to perform any of the methods of described herein is provided.

DETAILED DESCRIPTION

The features described are generally applicable to the field of flow cytometry, such as in applications that require the quantitative assessment of the median fluorescence intensity (MFI), which consequently requires reagents with tight MFI tolerances. The latter requires manufacturing the reagents under tight MFI control, which is an extremely difficult, lengthy, and costly process that does not even guarantee the minimization of MFI variability due to reagents lot-to-lot manufacturing variability. While reference is made specifically to MFI of a reagent, other variable reagent characteristics such a light scatter forward scatter (FSC); side scatter (SSC)), the peak fluorescence wavelength of a reagent, and the fluorescence decay time may be calibrated via the aspects described.

Described in further detail below are methods and systems for creating a set of correction factors for a set of flow cytometry reagents and subsequently using these factors to numerically adjust the data measured from a test sample to reduce variability that may be caused by lot-to-lot differences in the manufacturing of the reagents.

The calibration factors may be used to scale and/or correct event data of the cytometry data. The factors may be applied before or after performing spectral overlap compensation for MFI event data. The calibration factors may be also applied as a factor in calculating the SOVs (spillover values) used to determine the compensated values. Furthermore, the calibration file may also include the lot manufacturing date and other values, which can be used to compensate for the natural decay in the reagent with time post manufacturing, One non-limiting advantage of the features described is facilitation of the reagent manufacturing process by relaxing the reagent specifications and manufacturing restriction, such as the MFI (median fluorescence intensity) specifications restrictions. Practically, this allows any reagent lot, with appropriate calibration, to meet the accuracy specifications required for population discrimination in the multidimensional classification space.

The new invention will help resolve some of the difficulties encountered in reagent manufacturing when tight response (e.g., MFI) control is desired. An example of these difficulties is that existing conjugates in panels are not designed for tight MFI control. For these panels, the chemistry processes are not validated for MFI control. Instead, the chemistry is validated to control yield. Another example of these difficulties is the scope of control needed to support multidimensional chemistries. In some implementations, the reagent may provide n-dimensional data to provide multiple layers of detection. This increases the factors which must simultaneously be controlled for a given reagent. An entire lot may be rendered useless if a manufacturing defect is identified in just one dimension.

Customers may also reap several non-limiting benefits from the described aspects. For example, once purchased, a reagent may be accurately calibrated over time. This can enhance the shelf-life of a given reagent thereby reducing waste and repurchasing needs. Furthermore, the standardization of the results can allow a body of knowledge to develop for a given assay. This allows meaningful comparisons of data across samples and over time. These comparisons, in turn, can lead to, for example, faster analysis of test results.

The described features obviates the need for complicated manufacturing processes needed to deliver reagents with tight specifications (e.g., fluorescence intensity) that are used to meet the accuracy requirements of multidimensional cytometry classification methods. Currently, there are very few single color products in flow cytometry that guarantee a consistent median fluorescence intensity (MFI) output. Flow cytometry reagents are meant as qualitative reagents optimized for the separation of negative from positive populations, not as a quantitative tool.

However, in recent years, flow cytometry reagents have been used with more quantitative purposes. These quantitative needs often rely on MFI as an output. As noted above, flow cytometry data, such as MFI event data, is very difficult to control due to the large number of variables involved in the manufacturing, conjugation and handling of fluorescent antibodies as well as the large variability that working with biological substances, like proteins and dyes brings.

Asking manufacturing to produce a product with consistent MFI from lot to lot is an immensely difficult task that would require strict controls at every step of the production process, making this extremely expensive and not cost effective. When thinking about a multicolor flow cytometry product, this problem is only made worse by spillover and interactions between different fluorochromes and conjugates, making MFI consistency almost impossible.

Instead of forcing the reagent (which has biological and chemical limitations) to fit within an desired specification, systems and methods to create a numerical correction factor that allows any lot of reagent manufactured that passes existing quality control specifications to still fit the desired specification are described. Since all functional testing performed in quality control uses the linear range of the instrument, this correction factor could be applied and generate a correct approximate result from any lot of reagent produced by manufacturing no matter how distant it is from the reference target reading. This numeric factor can be generated as a deviation from a reference value, and applied mathematically through a module implemented via software, hardware, or a hybrid of these to each particular lot of reagent made. This applies not only to single color reagents, but also to multicolor products. This correction factor could not only be applied to correct MFI variations resulting from lot to lot differences in manufacturing, but could also help with spillover correction and even account for activity decay of the reagent over time.

As used herein, "system" and "instrument" and "apparatus" generally encompass both the hardware (e.g., mechanical and electronic) and associated software (e.g., computer programs) components.

As used herein, an "event" generally refers to the data measured from a single particle, such as cells or synthetic particles). Typically, the data measured from a single particle are include a number of parameters, including one or more light scattering parameters, and at least one fluorescence intensity parameters. Thus, each event is represented as a vector of parameter measurements, wherein each measured parameter corresponds to one dimension of the data space.

Figure 1:
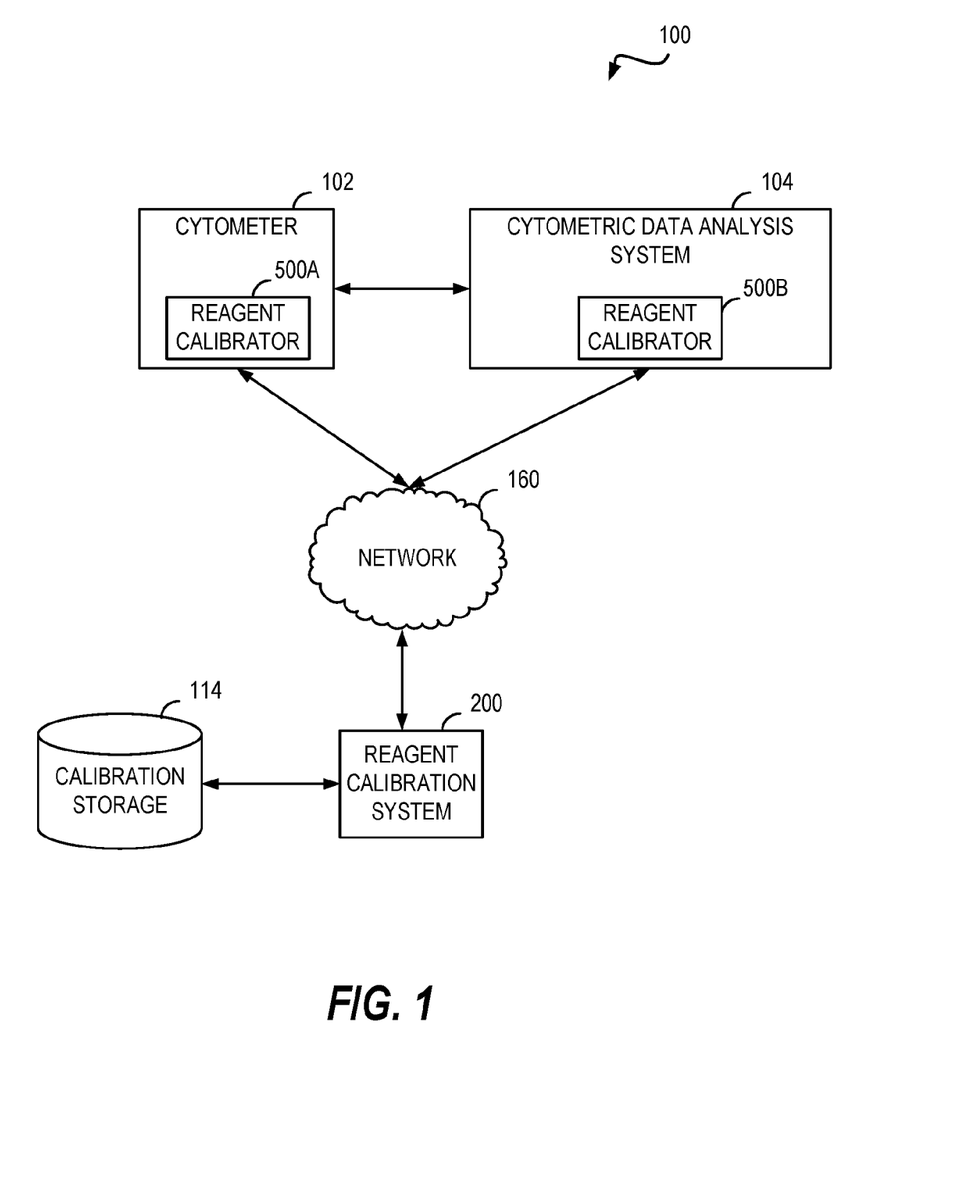
FIG. 1 shows a functional block diagram of a system for reagent calibration.

FIG. 1 shows a functional block diagram of a system for reagent calibration. The system 100 includes a cytometer 102. The cytometer 102 may be a flow and/or scanning cytometer such as those commercially available from, for example, BD Biosciences (San Jose, Calif.). The cytometer 102 may be configured to receive a biological sample along with one or more reagents. Using the received sample and reagent(s), the cytometer 102 may generate event data. The event data may include one or more events which represent a reading for a particular portion (e.g., cell) of the sample. One example reading is a median fluorescence intensity (MFI). The event data may include an identifier for the reagent used to generate the event data. The event data may include a lot identifier for the reagent indicating which manufacturing lot of the reagent was used to generate the event data. The event data may further include one or more contextual information elements such as the time the event data was generated, date on which the event data was generated, geospatial location where the event data was generated, instrument used to generate the data, instrument configuration information for the cytometer used to generate the event data, or operator who performed the experiment.

The cytometer 102 may provide the event data to a cytometric data analysis system 104. The cytometric data analysis system 104 is configured to process and analyze the event data. For example, analysis may include identifying a "population" or "subpopulation" of particles, such as cells or other particles, representing a group of particles that possess optical properties with respect to one or more measured parameters such that measured parameter data form a cluster in the data space. Populations may be recognized as clusters in the data. A cluster may be defined in a subset of the dimensions, e.g., with respect to a subset of the measured parameters, which corresponds to populations that differ in only a subset of the measured parameters. The pattern of clusters (e.g., number, location, size) can be used to identify pathological outcomes, such as a type of cancer. The cytometric data analysis system 104 may be configured to "gate" the event data. Gating generally refers to defining a set of boundary points identifying a subset of data of interest. In cytometry, a gate may bound a group of events of particular interest. As used herein, "gating" generally refers to the process of defining a gate for a given set of data. The cytometric data analysis system 104 may be configured to pre or post process event data such as formatting, unit conversion, standardization, encryption, or the like.

The cytometric data analysis system 104 may be implemented as data analysis software or data acquisition software executable by a processor on a computing device. The cytometric data analysis system 104 may be implemented as a stand-alone data scaling application. In such implementations, the cytometric data analysis system 104 may provide as an executable module or as a networked based service. The cytometric data analysis system 104 may be implemented in firmware and configured to perform one or more of the features described herein. In some implementations, the cytometric data analysis system 104 may be integrated with the cytometer 102.

The cytometer 102 and the cytometric data analysis system 104 shown in FIG. 1 each include a reagent calibrator 500A and 500B (collectively and individually referred to hereafter as reagent calibrator 500). The reagent calibrator 500 is configured to obtain one or more event data calibration factors to adjust collected event data. The reagent calibrator 500 is described in further detail below, such as in reference to FIG. 5.

The cytometer 102 may be configured to communicate directly with the cytometric data analysis system 104. In some systems, the cytometer 102 and the cytometric data analysis system 104 may communicate with each other and other systems via a network 160.

Examples of the network 160 include a wide area network (WAN), metropolitan area network (MAN), local area network (LAN), wireless local area network (WLAN), or personal area network (PAN). Although shown as one network, the network 160 may include several interconnected networks. The networks which may be included in the system 100 may differ according to the switching and/or routing technique used to interconnect the various network nodes and devices (e.g., circuit switching vs. packet switching), the type of physical media employed for transmission (e.g., wired vs. wireless), and the set of communication protocols used (e.g., Internet protocol suite, SONET (Synchronous Optical Networking), Ethernet, etc.). Regardless of the form the network 160 may take, the network 160 is configured to facilitate machine-to-machine messaging for reagent calibration as described in further detail herein.

The system 100 of FIG. 1 includes a reagent calibration system 200 as one example of another system the cytometer 102 and the cytometric data analysis system 104 may exchange communications. In some implementations, the reagent calibrator 500 is configured to process the communications for the associated cytometer or cytometric data analysis system. The reagent calibration system 200 is configured to generate and provide reagent calibration information as described in further detail below. The calibration information may be stored in a calibration storage 114 included in the system 100. In some implementations, the calibration storage 114 may be accessed via the network 160. In such implementations, the calibration storage 114 may be implemented as a cloud storage device. The calibration storage 114 may include a database or other information storage system to facilitate efficient storing and retrieving of calibration information.

Figure 2:
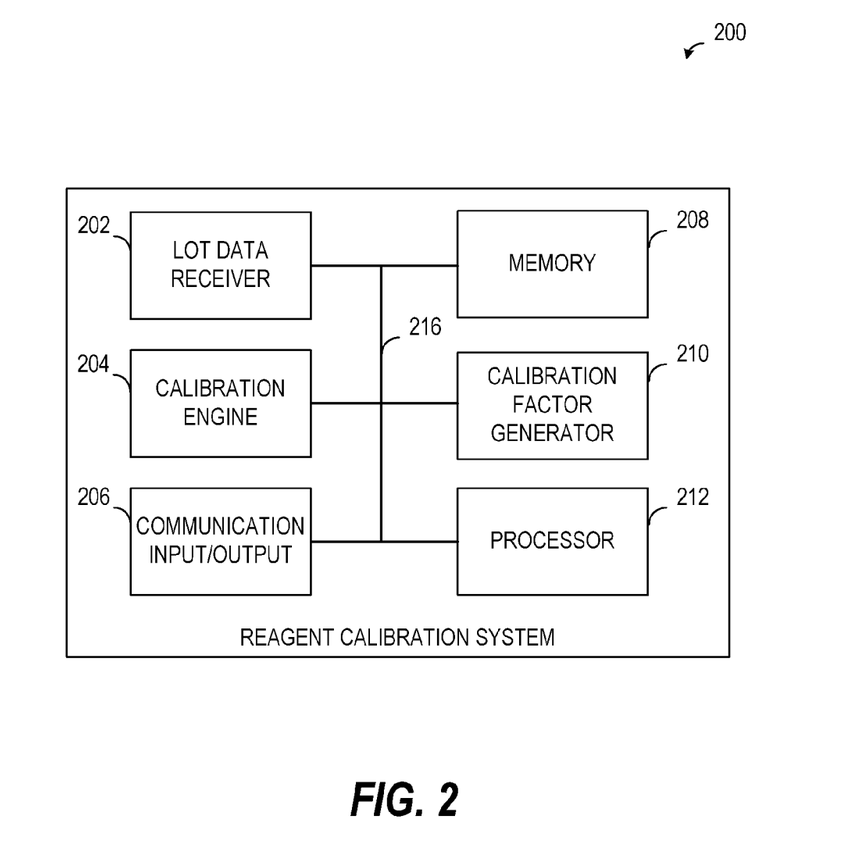
FIG. 2 illustrates a functional block diagram of an example of a reagent calibration syste

FIG. 2 illustrates a functional block diagram of an example of a reagent calibration system. The reagent calibration system 200 may be configured to receive a manufactured lot of a reagent and generate one or more calibration factors for the lot. The reagent calibration system 200 may be configured to receive a request for calibration factors associated with a specified reagent lot.

To generate the calibration factors, the reagent calibration system 200 includes a lot data receiver 202. The lot data receiver 202 is configured to receive event data for a particular manufactured lot of a reagent. The event data may be received via a communication input/output 206.

The communication input/output 206 may be configured to transmit and receive messages through wired or wireless communication channels. In one implementation, the communication input/output 206 may comprise a network card. The communication input/output 206 may provide the received information to an element included in the reagent calibration system 200. In some implementations, the communication input/output 206 may store the received information in a memory 208.

The memory 208 may include both read-only memory (ROM) and random access memory (RAM). The memory 208 may provide instructions and data to the processor 212. A portion of the memory 208 may also include non-volatile random access memory (NVRAM).

The reagent calibration system 200 may include a processor 212 which controls operation of the reagent calibration system 200. The processor 212 may also be referred to as a central processing unit (CPU). The processor 212 may perform logical and arithmetic operations based on program instructions stored within the memory 208. The instructions in the memory 208 may be executable to implement aspects of the methods described herein. The elements included in the reagent calibration system 200 may be coupled by a bus 216. The bus 216 may be a data bus, communication bus, or other bus mechanism to enable the various components of the system 200 to exchange information. It will further be appreciated that while different elements have been shown, multiple features may be combined into a single element, such as a calibration factor generator and calibration engine into a single calibration component.

The lot data receiver 202 may be configured to determine whether calibration factors have already been developed for the specified reagent and/or lot. If no factors have been generated, the lot data receiver 202 may determine that the lot data will be the reference lot. The determination may be based on information included in the lot data received. For example, the lot data may include a value indicating the lot data is a reference lot. The value may be provided, in one implementation, via a header field. The determination may be based on additional input information. For example, the lot data receiver 202 may provide a message for presentation to an operator indicating no calibration exists for the specified reagent and requesting either re-identification of the reagent or confirmation to use the lot data as a reference lot.

A calibration factor generator 210 may obtain the lot data and generate one or more calibration factors for the reagent lot. If the lot is a reference lot, the calibration factors may include assigning a calibration formula for the reagent. For example, the reagent may provide four dimensions of spectral data. Accordingly, the reagent may be associated with an equation including four terms, one for each dimension. The equation may be provided via an input device or retrieved from a library of stored terms and equations. The equation may include contextual adjustments such as: time from date of manufacture, environment (e.g., temperature, humidity, barometric pressure), instrument type, instrument configuration, and instrument state (e.g., temperature, available memory, available processor power, schedule), instrument operator.

If the lot is not a reference lot, the calibration factor generator 210 is configured to retrieve the calibration information, if any, and event data for the reference lot of the identified reagent. By comparing the event data from the reference lot to the measured event data from the manufactured lot under test, the specific factors needed to align the measured event data with the reference event data may be generated. The factors may be expressed, in one implementation, as a deviation from a reference value. The calibration factor generator 210 may be configured to include context information as part of the generation of the calibration factors for a given lot.

The factors generated by the calibration factor generator 210 may be stored in the memory 208. In some implementations, the factors may be stored in the calibration storage 114 shown in FIG. 1. The calibration factor generator 210 may be configured to store the calibration information in association with one or more identifiers for the reagent and manufacture lot used to generate the calibration information.

Figure 3:
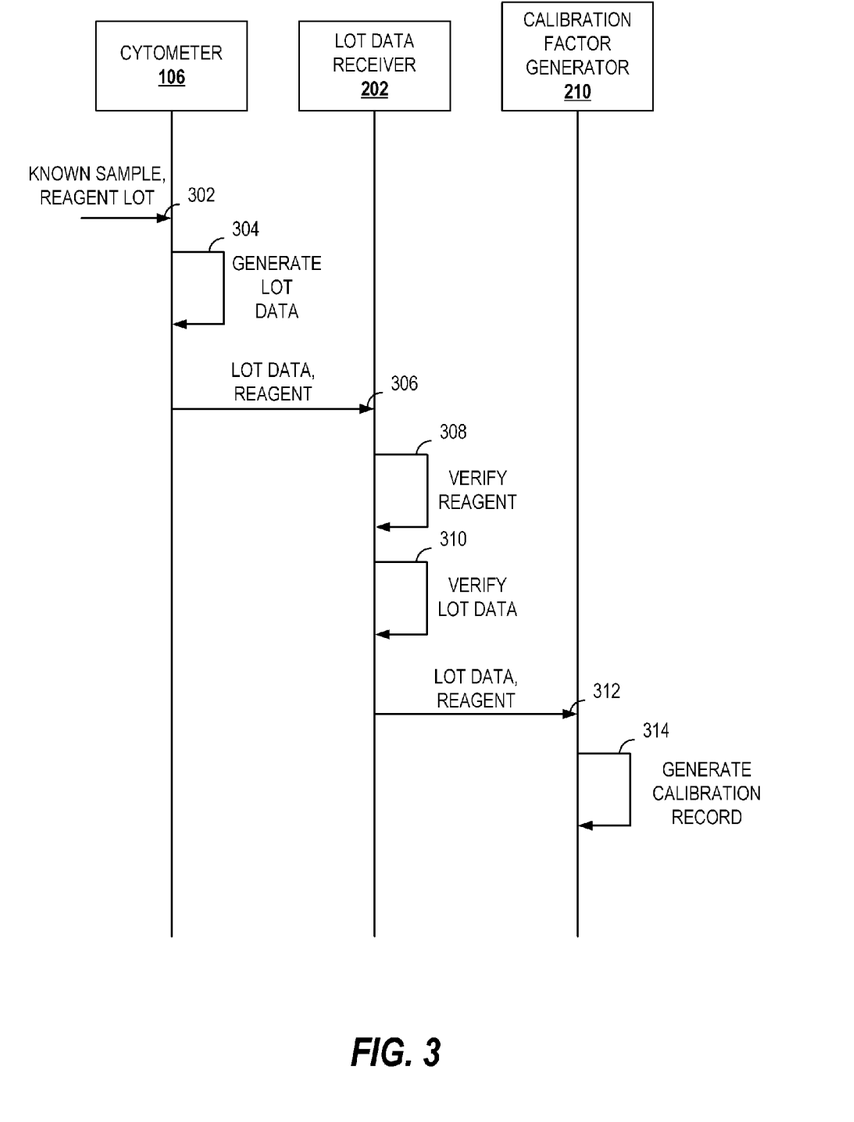
FIG. 3 illustrates a call flow diagram of an example message exchange for generating calibration information for a lot of a reagent.

FIG. 3 illustrates a call flow diagram of an example message exchange for generating calibration information for a lot of a reagent. FIG. 3 shows messages exchanged between several entities which may be configured for reagent calibration. It will be understood that other entities may be included as intermediaries but have been omitted from FIG. 3 for clarity purposes only.

At message 302, the cytometer 102 receives a known sample and a reagent from a manufacturing lot. The cytometer 102, at message 304, generates the event data for the lot. The event data may include, for example, MFI event information. The cytometer, at message 306, transmits the lot data and reagent identification to the lot data receiver 202. In some implementations, the cytometer 102 may be configured to transmit context information as described above for the lot. The lot data receiver 202, at message 308, verifies the reagent information. Verification may include determining whether the identified reagent is a valid reagent (e.g., a reagent for which the system can provide calibration). This verification may include processing the reagent identification information such as via a hashing algorithm, to determine the validity of the reagent's identity. Verification may include determining whether a reference lot has already been received for this reagent. If so, the lot data receiver 202 may terminate the process with a message indicating the presence of a previous reference lot or continue evaluation of the lot data as a manufacture lot for which calibration factors will generated to align the manufactured lot with a previously processed reference lot.

The lot data receiver 202, at message 310, may be configured to verify the lot data. Lot data verification may include verifying the authority of the information to serve as a lot for calibration. For example, an authorization token may be included in the lot data. indicating the data is trusted for the purpose of defining calibration information. The authority may be based on an identifier for the cytometer generating the lot data. For example, it may be desirable to only accept reference data lots from specifically configured and/or located cytometers. Verification may include ensuring the operator of the cytometer 106 is authorized to submit lot data. Lot data verification may include determining the sufficiency of the lot data to serve as a reference lot or sufficient to calibrate. For example, it may be desirable to require a minimum number of events in a given set of lot data to serve as a reference lot or lot which can reliably be used to generate calibration factors. If the lot data fails verification, the lot data receiver may terminate the process with a message indicating the deficiency with the provided lot data.

Having verified the reagent and the data, at message 312, the lot data receiver 202 provides the lot data and reagent information to the calibration factor generator 210. The calibration factor generator 210 is configured to generate, via message 314, the calibration record for the reference lot. Generating the record may include generating a unique identifier for the reagent lot. The process terminates, in some implementations, with a message indicating successful creation of the calibration record for the lot. In some implementations, this message may also include the identifier for the calibration record.

The calibration factors or the identifiers to obtain the factors may be provided along with the reagent to customers.

For example, the reagent may be shipped with a non-volatile computer readable media (e.g., CD-ROM, DVD-ROM, USB memory stick, floppy disk, Secure Digital card) which include the calibration information for the reagent lot. In some implementations, a customer may use the identifier to obtain the calibration information. For example, a code may be included on the reagent which can be transmitted to the reagent calibration system 200. Via the communication input/output 206, the reagent calibration system 200 receives the code and a calibration engine 204 determines which calibration factors to provide. The calibration engine 204 may determine the calibration factors to provide by decoding the input code information to determine the reagent and lot of interest. Using the reagent and lot information, the calibration engine 204 may perform a lookup for the calibration information. In some implementations, calibration engine 204 may be configured to adjust the calibration information. For example, because time may be a calibration factor, one or more elements included in the calibration information may need further refinement due to a different between when the factor was generated and the time at which the factor is requested. The calibration information may be transmitted to the requesting device via the communication input/output 206.

Figure 4:
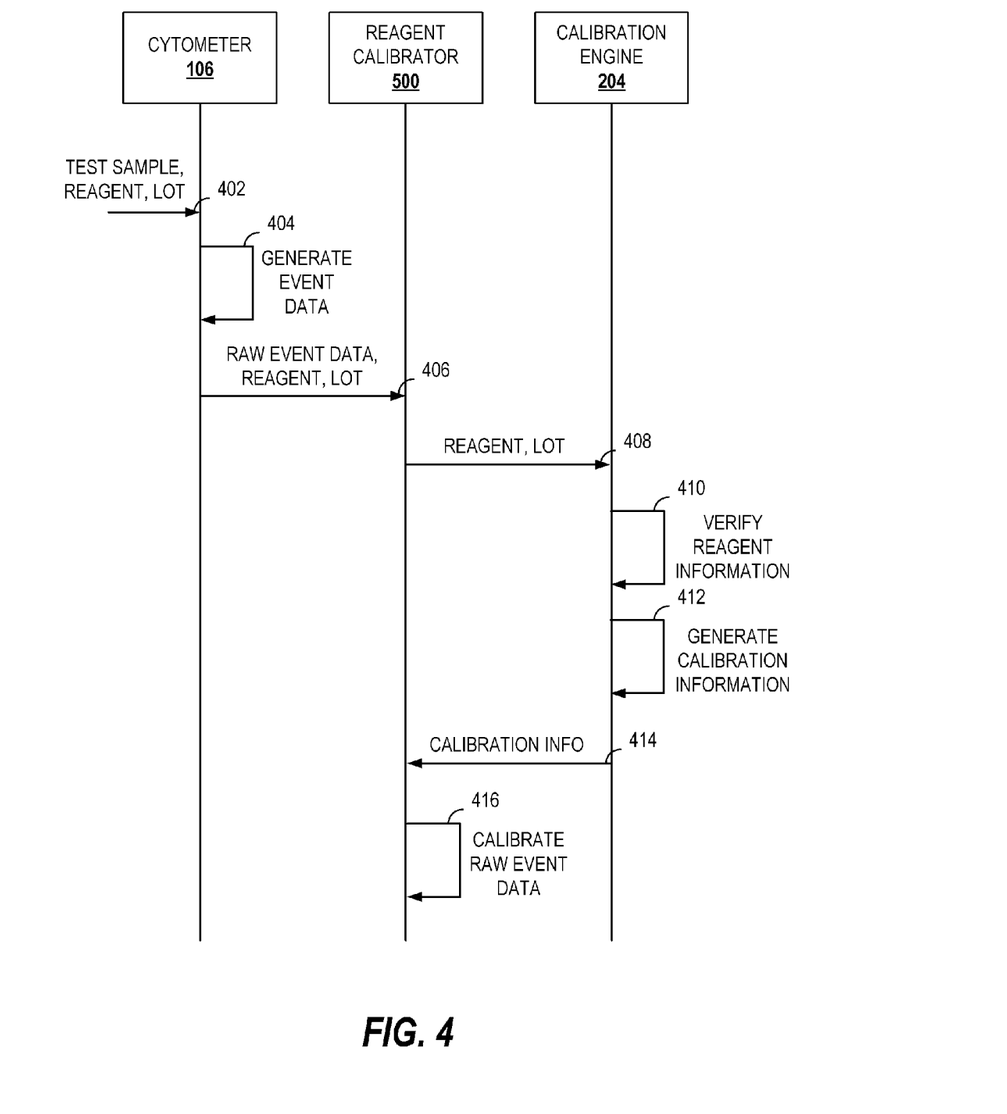
FIG. 4 illustrates a call flow diagram of an example message exchange for calibrating cytometric data obtained using a lot of a reagent.

FIG. 4 illustrates a call flow diagram of an example message exchange for calibrating cytometric data obtained using a lot of a reagent. FIG. 4 shows messages exchanged between several entities which may be configured for reagent calibration. It will be understood that other entities may be included as intermediaries but have been omitted from FIG. 4 for clarity purposes only.

At message 402, a test sample treated with an identified lot of a reagent is provided to the cytometer 106. The cytometer 106 may be the same cytometer used to generate the calibration information or a different cytometer, such as one located at a reagent customer's laboratory.

The cytometer 106, via message 404, executes the specified test to generate event data. The event data may include median fluorescent intensity information for events.

The raw event data may be provided, via message 406, to the reagent calibrator 500. The reagent calibrator 500 may also receive information identifying the reagent and lot used to generate the raw event data.

Message 408 may be transmitted from the reagent calibrator 500 to the calibration engine 204. The message 408 may include the information identifying the reagent and lot. In some implementations this may be the identifier provided with the reagent, as discussed above.

The calibration engine 204, at message 410, verifies the reagent information. Verification of the reagent information may include determining whether calibration information exists for the specified reagent and/or lot. In some implementations, it may be desirable to provide the calibration information on a subscription basis to authorized users. In such implementations, verification may include identifying an authorization value and determining whether the value is permitted to receive the requested calibration information, in whole or in part. If the verification fails, a message (not shown) may be provided including a value indicating the error.

If verified, at message 412, calibration information for the requested reagent lot is generated. Generating the calibration information may include looking up the calibration information from the calibration storage 114. In some implementations, further refinement of the calibration information in the calibration storage 114 may be performed by the calibration engine 204 to account for dynamic information such as time elapsed since manufacture of the lot. The calibration information may be stored in a cache of the calibration engine 204. In such implementations, before performing lookups or computations to produce the calibration information, the calibration engine 204 may consult a cache memory for the requested information. Conventional caching algorithms may be implemented to manage the cache memory space such as access frequency based caching or random replacement caching, Once generated, the calibration information is sent to the reagent calibrator 500 via message 414. The reagent calibrator 500 may then calibrate the raw event data to generate calibrated event data at message 416. The calibrated event data may be transmitted to another entity or stored for further processing. In some implementations, the raw event data may be stored along with the calibrated event data. In some implementations, the raw event data may be stored along with the calibration information. In some implementations, the calibrated event data along with the calibration information may be stored.

Figure 5:
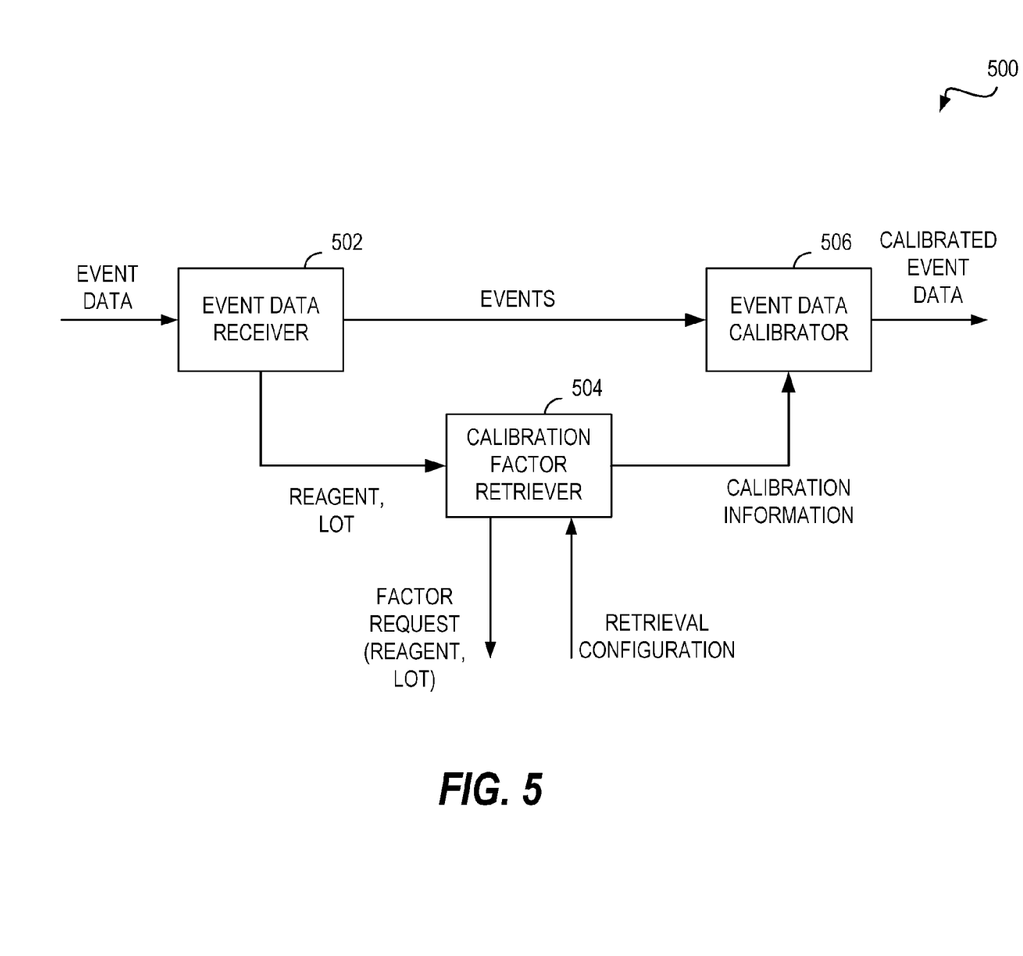
FIG. 5 shows a functional block diagram of an example reagent calibrator.

FIG. 5 shows a functional block diagram of an example reagent calibrator. The reagent calibrator 500 includes an event data receiver 502. The event data receiver 502 is configured to receive the raw event data. When integrated in a flow cytometer, such as the reagent calibrator 500A, the raw event data may be provided from a sample analysis module of the cytometer. In some implementations, the event data receiver 502 may receive the raw event data from memory or as streaming data. The event data receiver 502 is further configured to identify the lot and reagent information from the received event data. The identification may include parsing one or more header fields of the event data to obtain an identifier for the reagent and/or lot.

The identification information for the reagent and lot are provided to a calibration factor retriever 504. The calibration factor retriever 504 is configured to retrieve calibration information for a given reagent lot. The retrieval process includes determining a source for the calibration information and initiating the communications with the source to retrieve the calibration information. For example, some calibration information may be provided via a non-volatile memory. In such implementations, the calibration factor retriever 504 may be configured to determine whether the volume including the calibration information has been mounted. A factor request may perform a look up on the volume or within a file included on the volume. In some implementations, the calibration information may be provided via network communications with a calibration engine. In such implementations, the calibration factor retriever 504 may be configured to generate and transmit a factor request to the calibration engine and receive the information sent in response. The factor request may include the information identifying the reagent and lot.

To facilitate the various retrieval mechanisms that may be used for various reagents, the calibration factor retriever 504 may receive a retrieval configuration. The retrieval configuration may identify the type of source and provide the information needed to communicate with the source. For example, if a volume should be mounted, a volume name may be specified in the configuration. As another example, if a calibration engine is used for obtaining the calibration information, endpoint information (e.g., URL, IP address) and security information (e.g., username, password, authorization token) may be included in the configuration.

The calibration factor retriever 504 provides the calibration information to an event data calibrator 506. The event data calibrator 506 also receives the events included in the event data. The event data calibrator then applies the calibration information to each event to generate calibrated event data.

Figure 6:
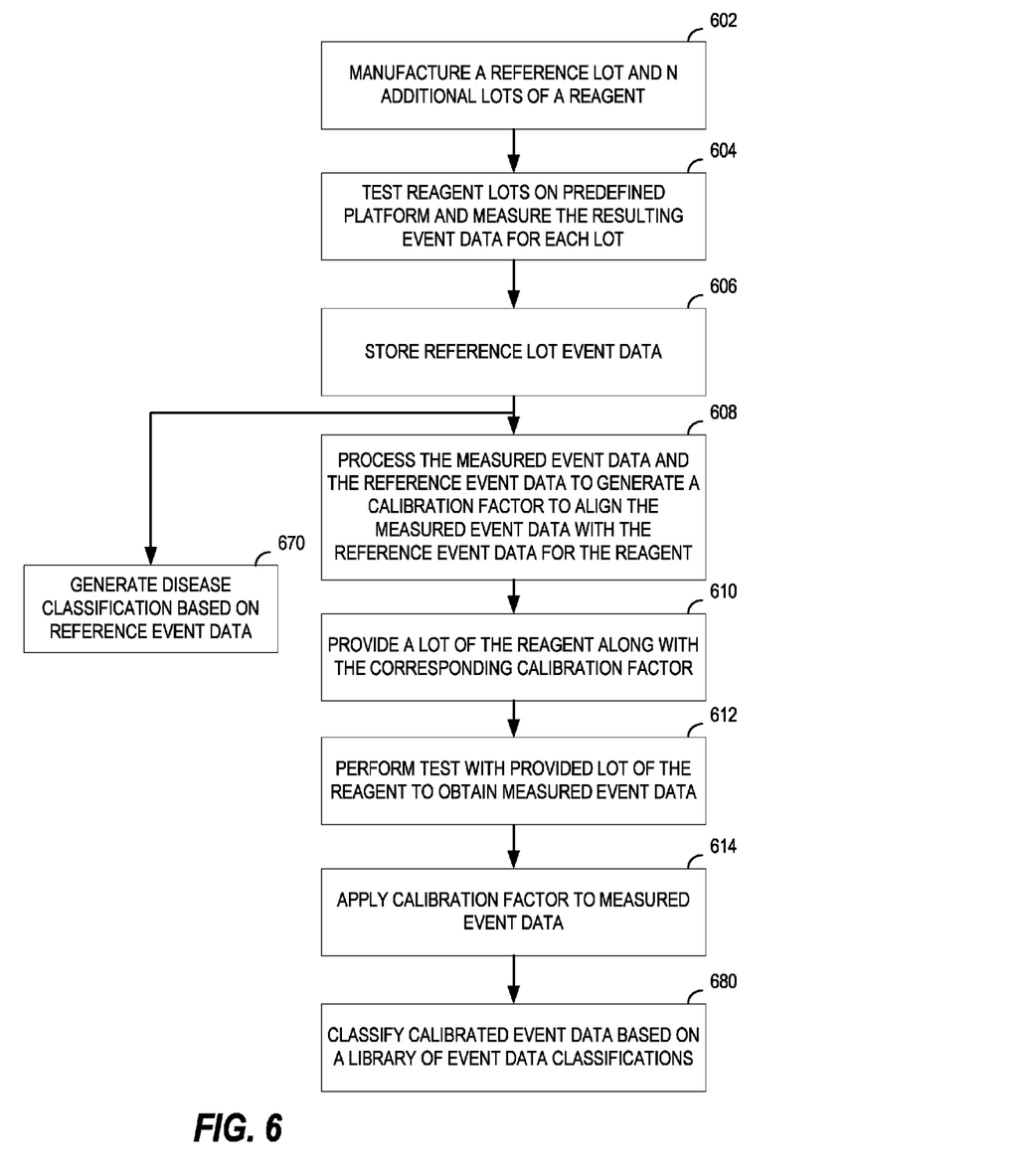
FIG. 6 shows a process flow diagram of a method of reagent calibration including aspect described above.

FIG. 6 shows a process flow diagram of a method of reagent calibration including aspect described above. The method may be implemented in whole or in part by the reagent calibrator 500 and the reagent calibration system 200.

At node 602 a reference lot and one or more additional lots of a reagent are manufactured. At node 604, the reagents are each tested on a known platform. The known platform includes a commonly configured cytometer and a known sample. The test measures event information such as median fluorescence intensity. At node 606, the reference lot event information is stored. At node 608, the measured event data for a non-reference lot is compared with the measured event data for the reference lot to generate a calibration factor. The calibration factor aligns the measured event data with the reference event data. In some implementations, the comparison may be the difference or ratio between the reference and the actual values obtain for testing the non-reference lot. Other information that could be included in this correction factor such as, for example, spill over into other channels and reagent stability decay expected over time. This correction factor is associated with the particular lot number (e.g., via a reagent lot file, a calibration engine).

In some implementations, it may be desirable to use a known sample from a pool of multiple donors such as a multi-donor blood pool. Using a multi-donor sample pool for reagent calibration can generate calibration factors with increased reliability because the factors would more closely represent differences in the MFI variability. Having a variety of biological sample sources can minimize the impact of the sample itself (e.g., inherent biological differences of person A's blood as compared to person B's blood) on the calibration factors. In one example implementation, the calibration factors can be obtained by testing both a new-lot reagent(s) and a previous-lot reagent on the same pool of multi-donor blood and then generating the calibration factors by comparing the MFI of the new-lot reagent to that of the previous-lot reagent.

At node 610, the lot of the reagent is provided along with the calibration information or identification information to obtain the calibration information. At node 612, a test is performed with the provided lot of reagent to obtain raw event data. At node 614, the calibration information is applied to the raw event data to generate calibrated event data.

One non-limiting advantage of the described calibration features is the ability to generate, such as via node 670, disease classifications based on the reference event data. Because event data may be consistently produced (e.g., calibrated), a classification library may be generated that can be used by researchers or other cytometric data analysis systems to analyze test data. Because the variation due to reagent lot can be minimized or eliminated using the calibration information, meaningful comparisons can be made between event data for different tests over time.

In such implementations, at node 680, the calibrated event data may be classified based on the library of classifications generated at node 670.

In an example embodiment the reagent(s) lot is tested against an established reference lot to determine the required calibration factors. This is followed by the generation of a calibration file including a lookup table of the calibration factors and the date of lot manufacturing. Cytometry data is acquired using the reagent(s) lot. The calibration file is then imported into the data analysis software and the cytometry data resulting from each reagent (e.g., MFI) is adjusted by the corresponding calibration values. Once calibrated, population classification may be performed to provide an accurate and fast analysis of the data.

When a customer receives a lot of the reagent, the correction factor could be applied manually by the user or in one embodiment, it could automatically be calculated and applied by the software based on the lot number and reagent lot file provided and the date the reagent is being used and acquired on the flow cytometer. The correction (calibration) factor(s) would then ensure that no matter how different the actual measured characteristic (e.g., intensity) caused by the reagent itself is coming out of manufacturing, the reagent measurement for a given lot will be normalized and its performance, as far as the characteristic is concerns, will be automatically matched to that of the expected reference against which it was calibrated.

The features described provide aspects which account for reagent characteristics which are highly variable and difficult to control due to the large number of factors that affect it, such as MFI. By generating and applying a correction factor calculated from a reference instead of having tight manufacturing specifications, any existing reagent that passes existing QC specifications could be used for characteristic controlled products, such as MFI controlled products, including multicolor panels. This reduces the burden on manufacturing and relaxes QC specifications because the calibrated characteristics are discrete measurable values that can be easily manipulated mathematically when acquired under linear range of the flow cytometer. It will be appreciated that the aspects described are not limited to linear relationships and may be applied for other calibration factors and/or equations. Since functional testing performed in QC typically uses the linear range of the instrument, the calibration information could be applied and generate a correct approximate result from any lot of reagent produced by manufacturing no matter how distant it is from the reference target.

Figure 7:
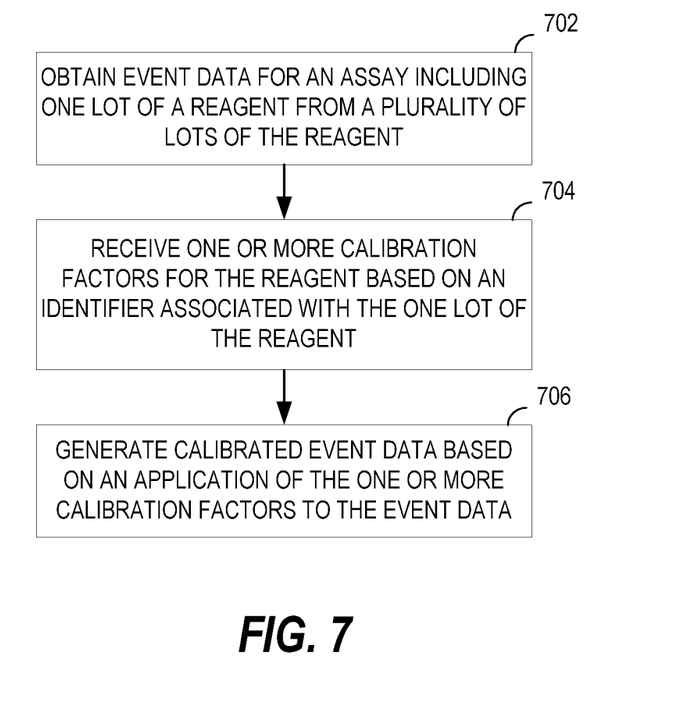
FIG. 7 shows a process flow diagram for a method of reagent calibration.

FIG. 7 shows a process flow diagram for a method of reagent calibration. The method may be implemented in whole or in part by the devices described herein such as the reagent calibrator 500.

At node 702, event data for an assay including one lot of a reagent from a plurality of lots of the reagent is obtained. Obtaining the event data may be receiving the event data at a flow cytometer or receiving stored event data at a flow cytometer or cytometric data analysis system. The event data may include multi-dimensional cytometric measurements such as median florescent intensity or spill over. At node 704, one or more calibration factors for the reagent is received. The calibration factors are received based on an identifier associated with the one lot of the reagent. Receiving the calibration factors may include receiving the calibration factors from a memory or via network messaging with, for example, a calibration engine. At node 706, calibrated event data is generated based on an application of the one or more calibration factors to the event data.

As used herein, the terms "determine" or "determining" encompass a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, establishing, and the like.

As used herein, the terms "provide" or "providing" encompass a wide variety of actions. For example, "providing" may include storing a value in a location for subsequent retrieval, transmitting a value directly to the recipient, transmitting or storing a reference to a value, and the like. "Providing" may also include encoding, decoding, encrypting, decrypting, validating, verifying, and the like.

As used herein, a phrase referring to "at least one of" a list of items refers to any combination of those items, including single members. As an example, "at least one of: a, b, or c" is intended to cover: a, b, c, a-b, a-c, b-c, and a-b-c.

Those of skill in the art would understand that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Those of skill in the art would further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The techniques described herein may be implemented in hardware, software, firmware, or any combination thereof. Such techniques may be implemented in any of a variety of devices such as general purposes computers, wireless communication devices, or integrated circuit devices having multiple uses including application in wireless communication device handsets and other devices. Any features described as modules or components may be implemented together in an integrated logic device or separately as discrete but interoperable logic devices. If implemented in software, the techniques may be realized at least in part by a computer-readable data storage medium comprising program code including instructions that, when executed, performs one or more of the methods described above. The computer-readable data storage medium may form part of a computer program product, which may include packaging materials. The computer-readable medium may comprise memory or data storage media, such as random access memory (RAM) such as synchronous dynamic random access memory (SDRAM), read-only memory (ROM), non-volatile random access memory (NVRAM), electrically erasable programmable read-only memory (EEPROM), FLASH memory, magnetic or optical data storage media, and the like. The computer-readable medium may be a non-transitory storage medium. The techniques additionally, or alternatively, may be realized at least in part by a computer-readable communication medium that carries or communicates program code in the form of instructions or data structures and that can be accessed, read, and/or executed by a computer, such as propagated signals or waves.

The program code may be executed by a processor, which may include one or more processors, such as one or more digital signal processors (DSPs), general purpose microprocessors, an application specific integrated circuits (ASICs), field programmable logic arrays (FPGAs), or other equivalent integrated or discrete logic circuitry. Such a processor may be configured to perform any of the techniques described in this disclosure. A general purpose processor may be a microprocessor; but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Accordingly, the term "processor," as used herein may refer to any of the foregoing structure, any combination of the foregoing structure, or any other structure or apparatus suitable for implementation of the techniques described herein. In addition, in some aspects, the functionality described herein may he provided within dedicated software modules or hardware modules configured for encoding and decoding, or incorporated in a combined video encoder-decoder (CODEC).

The methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may he modified without departing from the scope of the claims.

Various embodiments of the invention have been described. These and other embodiments are within the scope of the following claims.

What is claimed is:

1. A method, comprising:
   obtaining, via an electronic device including a processor, event data for an assay including a reagent, said reagent associated with one of a plurality of manufacturing lots of the reagent;
   detecting, via the electronic device, an identifier affixed on a vessel including said reagent, wherein the identifier is associated with the one of the plurality of manufacturing lots;
   transmitting, via a network, a request for one or more calibration factors for said reagent, wherein the request includes the identifier;
   receiving, from the network, the one or more calibration factors for the one of the plurality of manufacturing lots of the reagent; and
   generating calibrated event data based on an application of the one or more calibration factors to the event data.

2. The method of claim 1, further comprising:
   calibrating a flow cytometer for the assay including the reagent, wherein the flow cytometer is calibrated using at least one of the one or more calibration factors; and
   analyzing, via the electronic device, a sample to generate the event data.

3. The method of claim 1, wherein receiving said one or more calibration factors includes:
   receiving a calibration factor for each dimension of spectral data detected using said reagent.

4. The method of claim 1, further comprising:
   storing said one or more calibration factors in a machine-readable medium; and
   retrieving said one or more calibration factors from the machine-readable medium.

5. The method of claim 1, wherein said one or more calibration factors include a mean fluorescence intensity calibration factor.

6. The method of claim 1, wherein the event data comprises flow cytometry event data.

7. The method of claim 6, wherein the flow cytometry event data includes median florescence intensity measurements.

8. A system, comprising:
an event data receiver configured to receive event data for an assay including a reagent, said reagent associated with one of a plurality of manufacturing lots of the reagent;
a calibrator configured to:
receive an identifier affixed on a vessel including said reagent, wherein the identifier is associated with the one of the plurality of manufacturing lots,
transmit, via a network, a request for one or more calibration factors for said reagent, wherein the request includes the identifier;
receive, from the network, the one or more calibration factors for the one of the plurality of manufacturing lots of the reagent; and
an event data processor configured to generating calibrated event data based on an application of the one or more calibration factors to the event data.

9. The system of claim 8, wherein the calibrator is further configured to calibrate a flow cytometer for the assay including the reagent, wherein the flow cytometer is calibrated using at least one of the one or more calibration factors.

10. The system of claim 8, wherein the one or more calibration factors includes a calibration factor for each dimension of spectral data detected using said reagent.

11. The system of claim 8, wherein said one or more calibration factors include a mean fluorescence intensity calibration factor.

12. The system of claim 8, wherein the event data comprises flow cytometry event data.

13. The system of claim 12, wherein the flow cytometry event data includes median florescence intensity measurements.

14. The system of claim 8, wherein the request includes an instrument identifier for an instrument collecting the event data, and wherein the one or more calibration factors include a contextual adjustment for the instrument associated with the instrument identifier.

15. The system of claim 14, wherein the contextual adjustment is based on at least one of: a temperature of the instrument, memory available to the instrument, processor power available to the instrument, or an assay schedule of the instrument.

16. The method of claim 1, wherein the request includes an instrument identifier for an instrument collecting the event data, and wherein the one or more calibration factors include a contextual adjustment for the instrument associated with the instrument identifier.

17. The method of claim 16, wherein the contextual adjustment is based on at least one of: a temperature of the instrument, memory available to the instrument, processor power available to the instrument, or an assay schedule of the instrument.

18. The method of claim 1, further comprising retrieving a calibration authorization value from a memory, wherein the request for the one or more calibration factors includes the calibration authorization value.

* * * * *